US00PP09858P

United States Patent [19]

Zaiger et al.

[11] Patent Number: Plant 9,858

[45] Date of Patent: Apr. 15, 1997

[54] PLUM TREE "HIROMI RED"

[76] Inventors: Chris F. Zaiger, 929 Grimes Ave.; Leith M. Gardner, 1207 Grimes Ave.; Gary N. Zaiger, 1907 Elm Ave.; Grant G. Zaiger, 4005 California Ave., all of Modesto, Calif. 95358

[21] Appl. No.: 585,725

[22] Filed: Jan. 16, 1996

[51] Int. Cl.[6] ..... A01H 5/00

[52] U.S. Cl. ..... Plt./38.1

[58] Field of Search ..... Plt./38.1

*Primary Examiner*—James R. Feyrer

[57] ABSTRACT

A new and distinct variety of plum tree *Prunus salicina*, which has the following desirable features that are outstanding in a new variety:

1. Heavy and regular production of fruit.
2. Fruit with good flavor and eating quality.
3. Fruit with a high degree of attractive red skin color.
4. Fruit with firm flesh, good storage and shipping quality.
5. Vigorous, upright growth.
6. Relatively uniform ripening of fruit throughout the tree.
7. Fruit holding firm on the tree 7 to 8 days after picking ripe.

1 Drawing Sheet

ORIGIN OF THE VARIETY

The present new and distinct variety of plum tree was originated by us in our experimental orchard located near Modesto, Calif., from an open pollinated seedling selection, field identification number 20EB314. The seedling selection (20EB314) originated from a cross between Nubiana Plum (non-patented) and Queen Rose Plum (non-patented). A large number of these open pollinated seedlings were grown and maintained under careful observation, during which time the present variety exhibited the distinct and desirable characteristics described above and was selected for asexual reproduction and commercialization.

ASEXUAL REPRODUCTION OF THE VARIETY

The present new variety of plum tree was asexually propagated by budding, as performed by us in our experimental orchard located near Modesto, Calif., and shows that such reproductions run true to the original tree and are established and transmitted through succeeding propagations.

SUMMARY OF THE VARIETY

The present new and distinct variety of plum tree is of large size, vigorous, upright growth and a productive and regular bearer of large, yellow flesh, clingstone fruit with good flavor and eating quality. The fruit is further characterized by having firm flesh with good handling and shipping quality, having an attractive red skin color, being relatively uniform in ripening throughout the tree and holding firm on the tree 7 to 8 days after picking ripe. In comparison to the pollen parent, Queen Rosa Plum (non-patented), the new variety blooms later in the spring and has firmer flesh with greater production of fruit. The fruit ripening approximately 7 t 8 days earlier in maturity.

PHOTOGRAPH OF THE VARIETY

The accompanying color photograph shows typical specimens of the foliage and fruit of the present new variety of plum tree, the upper and lower surface of the leaves being illustrated, an exterior and cross sectional view of the fruit divided in the suture plane to reveal flesh coloration, pit cavity and a stone remaining in place. The photograph was taken shortly after being picked at maturity (firm ripe) and the colors are as nearly true as is reasonably possible in a color representation of this type.

DESCRIPTION OF THE VARIETY

The following botanical, detailed description of the present new and distinct variety of plum tree, its flowers, foliage and fruit are based on observations of specimens grown near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Form.*—Upright.
- *Density.*—Medium dense.
- *Production.*—Productive.
- *Bearer.*—Regular.

Trunk:
- *Size.*—Medium to large.
- *Texture.*—Medium shaggy.
- *Color.*—Brown to grayish brown (5-E-4) to (5-E-5).

Branches:
- *Size.*—Medium.
- *Texture.*—Smooth to medium rough.
- *Lenticels.*—Numerous. Small size.
- *Color.*—Light brown to brown (5-D-8) to (5-E-8). Varies with age of growth.

Leaves:
- *Size.*—Large. Average length — 4¾". Average width — 2".
- *Margin.*—Double serrate.
- *Petiole.*—Medium length. Medium thickness.
- *Form.*—Oblanceolate, pointed.
- *Texture.*—Smooth.
- *Thickness.*—Medium.
- *Glands.*—Number varies from 0 to 4. Average number 2. Globose. Primarily positioned on upper portion of petiole, with few on base of leaf blade.
- *Color.*—Upper surface — green to dark green (29-F-5) to (29-F-7). Lower surface — dull green to green (29-E-5) to (29-E-6).

Flower buds:
- *Size.*—Medium.
- *Length.*—Medium.
- *Form.*—Plump.

Flowers:

*Blooming period.*—Date of first bloom Mar. 1, 1994. Date of last bloom Mar. 8, 1994. Varies slightly with climatic conditions.

*Size.*—Medium.

*Pollen.*—Present.

*Color.*—White.

Fruit:

*Maturity when described.*—Firm ripe.

*Date of first picking.*—Jun. 21, 1994.

*Date of last picking.*—Jun. 25, 1994.

*Size.*—Large. Comparatively uniform. Average diameter axially 2½". Average transversely in suture plane2½".

*Form.*—Nearly globose, slightly flattened at stem end.

*Suture.*—Shallow, extends from base to apex.

*Ventral surface.*—Usually rounded.

*Cavity.*—Rounded. Average length ⅛". Average breadth ¼".

*Base.*—Retuse.

*Apex.*—Usually round, varies from slight tip to retuse.

*Stem.*—Medium thickness. Medium length.

Flesh:

*Ripens.*—Evenly.

*Texture.*—Firm.

*Juice.*—Moderate.

*Fibers.*—Small, tender.

*Flavor.*—Good, mild, good balance between sugar and acid.

*Aroma.*—Very slight.

*Eating quality.*—Good.

*Color.*—Light yellow to yellow (3-A-3) to (3-A-5). Pit cavity — yellow to dark yellow (4-A-4) to (4-B-6).

Skin:

*Thickness.*—Medium.

*Texture.*—Medium, tenacious to flesh.

*Tendency to crack.*—None.

*Bloom.*—Moderate.

*Down.*—Wanting.

*Color.*—Ground color — salmon to pastel red (6-A-4) to (7-A-4). Nearly overspread with madder red to bronze red (10-B-7) to (10-C-8). Speckled, small lighter colored dots randomly spaced.

Stone:

*Type.*—Clingstone.

*Size.*—Medium. Average length 1⅛". Average width ¾". Average thickness ½".

*Form.*—Ovate.

*Base.*—Varies from straight to rounded.

*Apex.*—Acuminate.

*Sides.*—Mostly equal, varies from equal to unequal.

*Surface.*—Slightly pitted throughout. Shallow furrows near stem end, one long furrow on each side of suture.

*Color.*—Light brown to brown (5-C-5) to (5-D-5).

Use: Dessert.

*Market.*—Local and long distance.

Keeping quality: Good. Good.

Shipping quality: Good.

The present new plum tree, its flowers, foliage and fruit may vary in slight detail due to climate, soil conditions and cultural practices under which the variety may be grown. The present description is that of the variety grown under the ecological conditions prevailing near Modesto, Calif.

We claim:

1. A new and distinct variety of plum tree, substantially as illustrated and described, characterized by its large size, vigorous, upright growth, being a productive and regular bearer of large, yellow flesh, clingstone fruit with good flavor and eating quality; the fruit is further characterized by having firm flesh with good storage and shipping quality, relatively uniform in ripening, and in comparison to Queen Rosa Plum (non-patented), the new variety has firmer fruit, heavier production and fruit ripening approximately 7 to 8 days earlier.

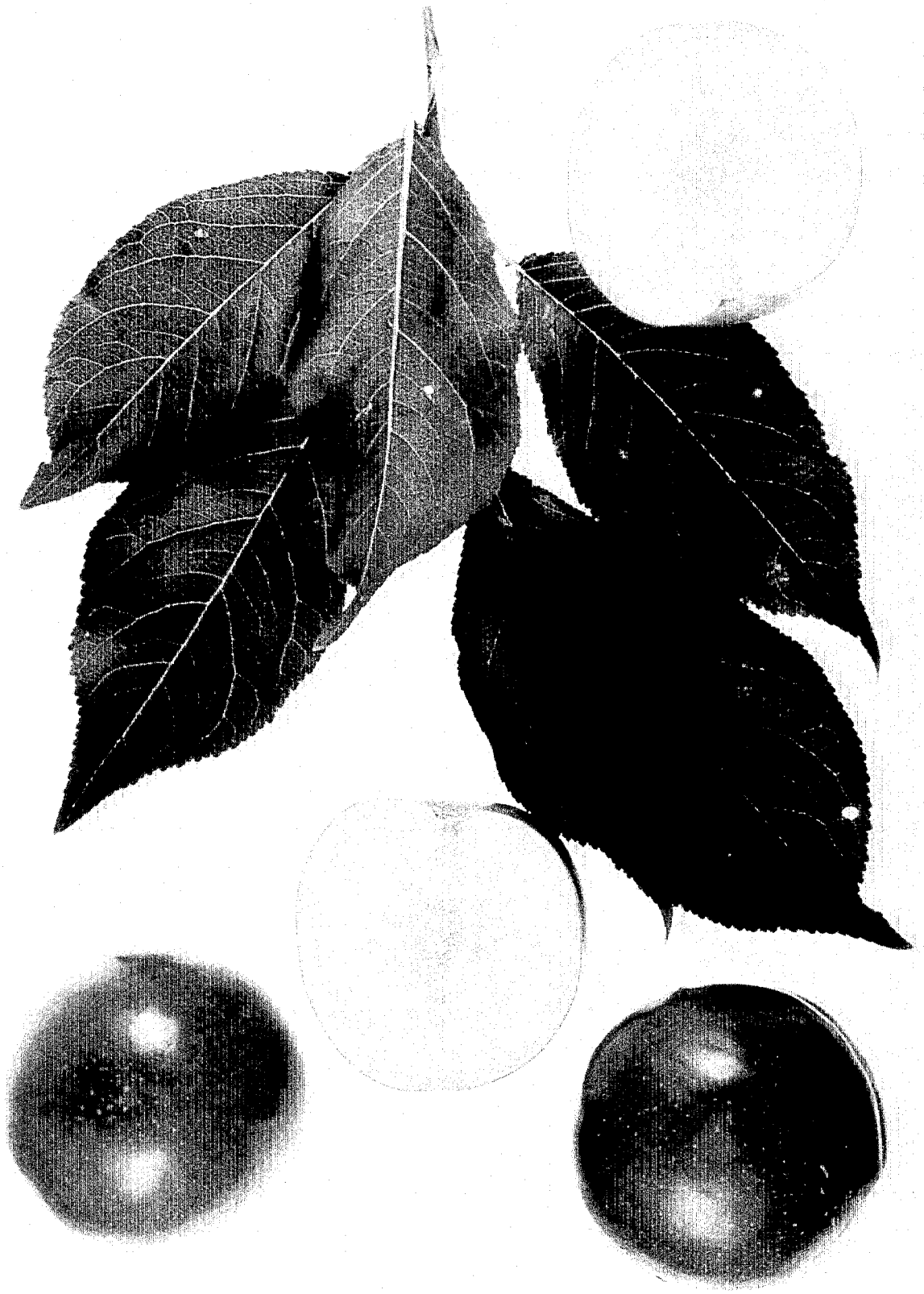

* * * * *